United States Patent [19]

Root et al.

[11] 4,200,690

[45] Apr. 29, 1980

[54] IMMUNOASSAY WITH MEMBRANE IMMOBILIZED ANTIBODY

[75] Inventors: David M. Root, Bedford; Francis X. Cole, Stow, both of Mass.

[73] Assignee: Millipore Corporation, Bedford, Mass.

[21] Appl. No.: 924,562

[22] Filed: Jul. 14, 1978

Related U.S. Application Data

[63] Continuation of Ser. No. 751,093, Dec. 16, 1976, abandoned.

[51] Int. Cl.² ..................... G01N 31/14; G01N 31/00
[52] U.S. Cl. ............................. 435/7; 435/28; 435/29; 435/174; 435/287; 435/288; 23/230 B; 23/915
[58] Field of Search ............... 195/103.5 A, 103.5 R, 195/63, 68, DIG. 11, 127, 99; 23/230 B, 915

[56] References Cited

U.S. PATENT DOCUMENTS

| | | | |
|---|---|---|---|
| 3,839,153 | 10/1974 | Schuurs et al. | 195/103.5 A |
| 3,951,748 | 4/1976 | Devlin | 195/103.5 R |
| 4,066,512 | 1/1978 | Lai et al. | 195/103.5 A X |

*Primary Examiner*—David M. Naff

[57] ABSTRACT

The presence of antigens is detected with a device having an antibody immunochemically reactive with the antigen bound to a first microporous membrane coated with an inert proteinaceous material and an antibody immunochemically non-reactive with the antigen bound to a second microporous membrane coated with an inert proteinaceous material. The device is particularly useful in an immunoassay for an antigen of *Entamoeba histolytica* in unfractionated feces or colon aspirate.

11 Claims, 2 Drawing Figures

IMMUNOASSAY WITH MEMBRANE IMMOBILIZED ANTIBODY

This is a continuation of application Ser. No. 751,093, filed Dec. 16, 1976, now abandoned.

RELATED APPLICATION

This invention makes use of the immobilization techniques that are disclosed and claimed in the copending, commonly assigned patent application of C. J. Lai, et al., Ser. No. 684,746, now published as German OS 2539657, now U.S. Pat. No. 4,066,512.

FIELD OF INVENTION

This invention relates to the detection of infections using immunological chemical reactions. More particularly, this invention is concerned with the detection of infections with intestinal parasites such as *Entamoeba histolytica* by the examination of stool samples.

BACKGROUND

Immunochemical methods have proven useful for the diagnosis of disease, especially where physical symptoms are ambiguous, asymptomatic carrier states exist, and where the causative agent is difficult to detect by conventional means. These methods have been most commonly used in the past in the examination of serum, lymph and cerebro-spinal fluid.

In the case of disease of the intestinal tract, immunochemical methods suitable for analysis of feces would be potentially useful. By way of example, such usefulness is especially apparent in diseases such as amoebiasis (amoebic dysentery), and giardiasis.

Amoebiasis is an infection of the bowel caused by the protozoan, *Entamoeba histolytica*. Its world-wide incidence, estimated as high as 50%, makes it a significant world health problem, especially in the underdeveloped countries. However, even in the United States, there is an estimated incidence of 3%, or approximately 6,000,000 infected persons.

Symptoms of infection are extremely variable. An infection may be asymptomatic or it may result in mild to severe diarrhea. Severe cases can result in ulceration of the large bowel mucosa, intestinal perforation and hemorrhage. Secondary invasion of other tissues, especially of the liver, occurs in some cases (less than 1%). The disease can be fatal. It is estimated that 90% of those infected by *Entamoeba histolytica* are asymptomatic carriers of the disease.

Diagnosis of the disease is complicated by the wide variety of symptoms it presents, many of which are common to other pathologic conditions. Methods of diagnosis employed in the prior art include both direct and indirect tests. Direct microscopic identification of the infecting organism in a patient's feces or in swabs or washings obtained from the rectum or sigmoid colon provides the best available positive diagnosis. Indirect diagnosis may be made by demonstrating the presence of antibodies against *Entamoeba histolytica* in the bloodstream.

In the direct method, a positive diagnosis can be made if the organism is identified in microscopic examination of the stool sample. Difficulties of three sorts are encountered with this method. First, the organism, in identifiable form, is often absent from the stools, even when the patient is suffering active symptoms. The reasons why the organism is only occasionally present are not fully understood, but relate in part to the organism's life cycle.

*Entamoeba histolytica* undergoes a complex life cycle in which it exists in morpholigically distinct forms. The identifiable form is termed a trophozoite, which is characterized by its appearance as a typical amoeboid cell, having a diameter of 10 to 60 microns, an irregular outline, and that is capable of movement by extensions of the cell body. Certain distinguishing cytological characteristics are also present which enable a trained technician to differentiate the organism from non-pathogenic amoebae. The organism may also exist in the form of a cyst and a precystic form. Cysts of *Entamoeba histolytica* are difficult to distinguish from those of non-pathogenic amoebae which sometimes inhabit the human gut, such as *Entamoeba coli* or *Entamoeba hartmanii*, in unstained specimens. A variety of environmental factors within the intestinal tract appears to contribute to the highly sporadic appearance of *Entamoeba histolytica*. Continuous examination of samples collected over a 6-day period may be required to obtain a sample having intact trophozoites.

A second difficulty with direct microscopic examination is due to the fact that trophozoites of *Entamoeba hartmanii* are cytologically distinguishable from *Entamoeba histolytica* only on the basis of size. Cells less than 10 microns in diameter are arbitrarily classified as *Entamoeba hartmanii* although some overlap in the size ranges of the two organisms may occur. Indeed, opinion is divided as to whether *Entamoeba hartmanii* and *Entamoeba histolytica* are in fact distinct species, although the appearance of *Entamoeba hartmanii* is generally associated with asymptomatic infections. The non-pathogenic *Entamoeba coli* is also difficult to distinguish microscopically from *Entamoeba histolytica*.

The third type of difficulty encountered is inherent in the nature of the material sampled. Interference may be encountered due to the presence of particulate matter in the feces, cell debris, clumps of bacteria, white blood cells, oil droplets and kaolin particles from medication taken to control diarrhea. Various techniques are available to remove such interfering materials, but always at the cost of increasing the duration and complexity of the diagnostic procedure. Furthermore, the fecal sample must be examined while fresh and still warm since the trophozoites round up and lose their characteristic morphology as the specimen cools.

Direct microscopic examination of stained specimens may also be employed. This procedure has the advantage that morphological characteristics are easier to see, which aids in the differentiation of *Entamoeba histolytica* from non-pathogenic amoebae and interfering particles. Stained slides may be several days in preparation and reading, however, and the requirement for samples taken on successive days is not avoided.

Direct microscopic examination of stained or unstained preparations must be carried out by a trained microscopist. The microscopist observes the specimen through a microscope while moving the slide slowly in order to bring all areas of the specimen into the field of view. Intense concentration is demanded. Fatigue drastically reduces efficiency and accuracy of observation after about an hour's viewing. The number of samples which can be processed by a microscopist in a given day is therefore limited. For background, see Brown, H. W., *Basic Clinical Parasitology*, Chap. 3, pp 18–37, (1975), and Katz, M., in *Postgraduate Medicine*, Vol. 58, p. 149, (1975).

Immunological Chemistry

For a better understanding of the present invention, a brief statement will be made as to the use that is made of immunological chemical reactions.

Antigen-antibody reactions occur in nature as part of the immunity system by which humans and other mammals combat the growth of foreign microorganisms. Most antigens are proteinaceous substances in whole or in part. A substance becomes an antigen by being introduced into an organism to which it is a foreign substance. For example, a protein comprising part of the cell surface of *Entamoeba histolytica* becomes an antigen when the organism invades man. The host organism has the capacity to distinguish foreign substances from endogenous substances, and the salient feature of the host organism's response is the formation of antibodies, which confer immunity against the foreign substance.

Antibodies are derived from a class of proteins found in serum, called immunoglobulins. When an antigen is presented to a host organism, an immunoglobulin is formed in response, having a capability of forming a specific combination with the antigen substance. Specifically, the reaction which takes place between an antigen and an antibody is a binding of one or more molecules of antibody to one or more molecules of antigen. Such a reaction is termed an immunochemical reaction. This binding is characterized by a high degree of specificity and a very low dissociation constant.

As a consequence of the high binding affinity (low dissociation constant) between antigens and antibodies, extremely sensitive methods for measuring the presence of one or the other of these components have been developed. Because of the high degree of specificity, immunochemical reactions are extremely valuable in the diagnosis and detection of disease. Such reactions differ from ordinary chemical reactions in that no chemical transformation occurs, such as a net gain or loss of reactive groups. Measurement of an immunochemical reaction depends, ultimately, on being able to distinguish the bound state of the reaction components from the unbound state. The technical difficulty of distinguishing between the bound and unbound states has impeded progress toward realizing the full potential of immunochemical reactions in medical diagnosis.

The detection of antibodies against specific foreign substances has been accomplished by a variety of methods in the prior art. These include hemaagglutination, latex particle agglutination, agar gel diffusion, complement fixation, counterelectrophoresis, fluorescent antibody techniques, and radioimmunoassay. The more sensitive of these methods have tended to require the use of expensive reagents and expensive equipment, which has limited their usefulness for routine diagnostic work. Moreover, like microscopic examination, such techniques generally require highly trained people and are usually very time consuming, in addition to being expensive.

Two recent advances in technology have occurred to increase the operating simplicity, speed and sensitivity of immunochemical assays. The first advance involved the development of techniques for coupling an immunologically reactive antigen or antibody to an insoluble carrier material. Thus, for example, an antibody immobilized on an insoluble carrier can, when exposed to a solution containing the antigen, bind the antigen and render it, in turn, immobilized. The entire complex of carrier, immobilized antibody, and bound antigen, can be then separated from the contaminating substances and unbound components, and subjected to analysis.

The second advance has been the development of techniques for conjugating an antibody to an enzyme in such a way that each retains its characteristic reactive properties. Thus, the antibody remains immunologically reactive, and the enzyme retains its catalytic activity. Such a conjugate can bind to an immobilized antigen, and the bound conjugate can be detected through the activity of the coupled enzyme.

These two techniques have been used in combination to develop a very sensitive type of assay termed an enzyme-linked immunosorbent assay. The present invention embodies these two basic techniques. For convenience, two types of enzyme-linked immunoassay will be discussed and referred to as EL-1 and EL-2; see the diagram below:

EL-1; C---Ab---Ag---Ab-Enz;
EL-2: C---Ag---Ab---AntiAb-Enz; where:
C represents an inert carrier;
Ab symbolizes antibody;
Ag symbolizes antigen;
C---Ab symbolizes carrier-bound (immobilized) antibody;
C---Ag symbolizes carrier-bound (immobilized) antigen;
Ab-Enz symbolizes the conjugate of an antibody with an enzyme; and
AntiAb-Enz symbolizes an antibody against immunoglobulin conjugated with an enzyme.

EL-1 is a technique for detecting the presence of an antigen. Antibody against the antigen is immobilized on an insoluble carrier. The immobilized antibody is then exposed to an antigen-containing fluid. The immobilized antibody harvests the antigen from the solution by binding it in place. The carrier is then separated from the solution, washed free of contaminants, and exposed to a solution of the antibody conjugated to an enzyme. The principle of operation is that the conjugate is able to bind only at sites occupied by the antigen, and that the number of sites so occupied determines the amount of conjugate which can bind. Each site where antigen is bound is thus tagged with bound enzyme whose presence is manifested by its ability to catalyze a reaction. The rate of such reaction is proportional to the amount of enzyme present and becomes a direct measure of the amount of antigen bound.

In EL-2, the component to be detected is an antibody. Antigen is immobilized on the carrier. Binding of the antibody is then measured by the subsequent binding of anti-immunoglobulin-enzyme conjugate. See Wisdom, G. B., in *Clinical Chemistry*, Vol. 22, p. 1243 (1976).

Methods for the detection of antibodies against *Entamoeba histolytica* in the serum of patients using the EL-2 method have been disclosed in a publication and a patient. See Devlin, U.S. Pat. No. 3,951,748 (April 20, 1976); and Bos, H. J., and van den Eijk, A. A., in *Transactions of the Royal Society of Tropical Medicine and Hygiene*, Vol. 69, p. 440 (1975). Their usefulness as diagnostic tools is limited by factors inherent in the use of measurement of circulating antibodies as a criterion for infection. First, previously infected patients may continue to have circulating antibodies to *Entamoeb histolytica* after the infection is cured. A positive response in that case cannot serve to eliminate the possibility of other etiology for the current symptoms. Second, asymptomatic carriers of *Entamoeba histolytica* often fail to have circulating antibodies to the organism so that their presence in the population as carriers of the disease cannot be detected by measuring circulating antibodies.

Since an estimated majority of persons infected with *Entamoeba histolytica* are asymptomatic, there is a large undetected reservoir of the organism in the general population. Such persons excrete cysts either primarily or exclusively, making their identification difficult. Paradoxically, it is the asymptomatic carriers who are the most contagious to others, since the excreted cysts of *Entamoeba histolytica* survive for long periods of time outside the human body, whereas trophozoites do not. Patients with active symptoms tend to excrete more trophozoites and fewer cysts. In consequence, a test capable of identifying asymptomatic carriers of *Entamoeba histolytica* would be highly desirable as a step toward eventual control of the spread of the disease.

Amoebic infections are amenable to chemotherapy. However, the drugs used to treat the disease have toxic side effects. Consequently, it is important to know not only whether the drug should be administered in the first place, but when treatment can be safely discontinued. One of the principal drugs used against amoebiasis, metronidazole, often causes diarrhea as a side effect, masking the effects of treatment. A diagnostic test useful in monitoring the course of treatment would be most desireable. In addition, the ability to identify *E. histolytica* specifically allows the doctor to prescribe drugs specific for the amoeba, instead of drugs with general specificity towards protozoa, which tend, in general, to be more toxic.

Because of the well-recognized difficulties in diagnosing amoebiasis, mistakes are frequently made. The disease is sometimes mistaken for ulcerative colitis, or for Crohn's disease. Such a mistaken diagnosis may result in needless and futile surgery. (See "Mimicry in Crohn's Disease," editorial in *The Lancet*, July 19, 1975, pp 115–116.)

SUMMARY OF THE INVENTION

The present invention relates to the diagnosis of a pathological condition manifested by the presence of an antigen. More specifically the antigen to be detected is determined using and assay of the EL-1 type whereby an antibody against the antigen that is to be detected is immobilized on an insoluble carrier coating on a surface, and incubated in the test sample under conditions where any antigen of the type to be tested is harvested by binding in an immunochemical reaction to the immobilized antibody. Any sites on the carrier where antigen is thus bound may in turn serve as binding sites for antibody-enzyme conjugate in which the antibody moiety is capable of binding to the antigen to be tested in a specific immunochemical reaction.

In the preferred embodiment, the invention is adapted to the detection of a diagnostic antigen in feces. A microporous membrane filter having immobilized antibody capable of immunochemically binding the diagnostic antigen is immersed in a suspension of feces for a time sufficient to permit harvesting of the antigen by immunochemical binding. The filter, mounted on a carrier to facilitate transfers and bearing harvested antigen on its surfaces, is then removed from the feces, washed to remove impurities and incubated in the presence of an antibody-enzyme conjugate. The conjugate is permitted to bind immunochemically at sites where any antigen has bound. After a second wash, to remove unbound conjugate, the filter, bearing bound conjugate, is incubated with a substrate of the enzyme. Preferably, the substrate is a chromagen, so that enzyme activity will be manifested by the appearance of color.

Used in this manner, the invention is believed to be the first instance of a diagnostic test for a pathological condition in which feces is directly analyzed for the presence of a specific antigen. The invention may be practiced in any condition where the presence of an antigen in the feces is diagnostic. By way of example the invention may be applied in the diagnosis of infections by parasitic protozoa such as *Entamoeba histolytica* and *Giardia lamblia*.

As applied to the detection of *Entamoeba histolytica* in a specimen of feces, the invention offers unique advantages over the prior art. Because the method is direct rather than an indirect assay of circulating antibodies, only those patients who are currently infected will give positive results. Furthermore, there is no need to draw a blood sample from the patient in order to perform the test. Because the invention operates by the detection of antigen rather than the appearance of certain morphologic forms of the organism, it is possible to detect the presence of the organism under conditions where trophozoites are not observable. Surprisingly, antigen can be detected in samples lacking any observable form of the organism. The invention has been found to be highly selective, capable of distinguishing the pathogenic *Entamoeba histolytica* from non-pathogenic *Entamoeba coli* and other amoebic species.

Additionally, secondary advantages arise as a consequence of the above-mentioned properties of the invention. Because antigen of the organism appears to be present in the feces of infected patients at times when intact organisms are not being excreted, the need to examine successive samples over a period of several days is obviated. More importantly, the invention offers for the first time the possibility of a rapid, practical method for detecting asymptomatic carriers of amoebiasis. The progress of treatment may be monitored by using the invention, so that toxic drug reactions may be minimized. As a further advantage, the practice of the invention involves simple manipulations and does not require specialized or expensive equipment or highly trained personnel. Since amoebiasis is especially prevalent in underdeveloped areas, this latter attribute of the invention is of major significance in adapting the invention for use in field clinics and remote hospitals. These attributes also make possible the manufacture of a test kit embodying the invention at a price compatible with its potential world-wide usefulness.

DRAWINGS

FIG. 1 is a front elevation of an immersible device that is constructed in accordance with one embodiment of the present invention and that is designed to harvest an antigen from a liquid containing it, such as, for example, from a fecal slurry containing the antigen of *Entamceba histolytica*, the device including a control, and FIG. 2 is a side elevation thereof.

DETAILED DESCRIPTION OF INVENTION

Figure 1:
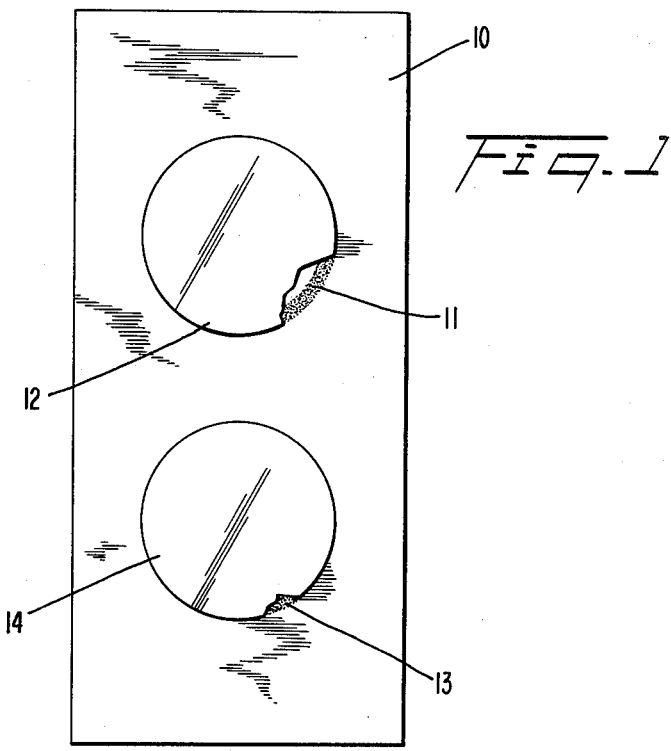
Figure 2:
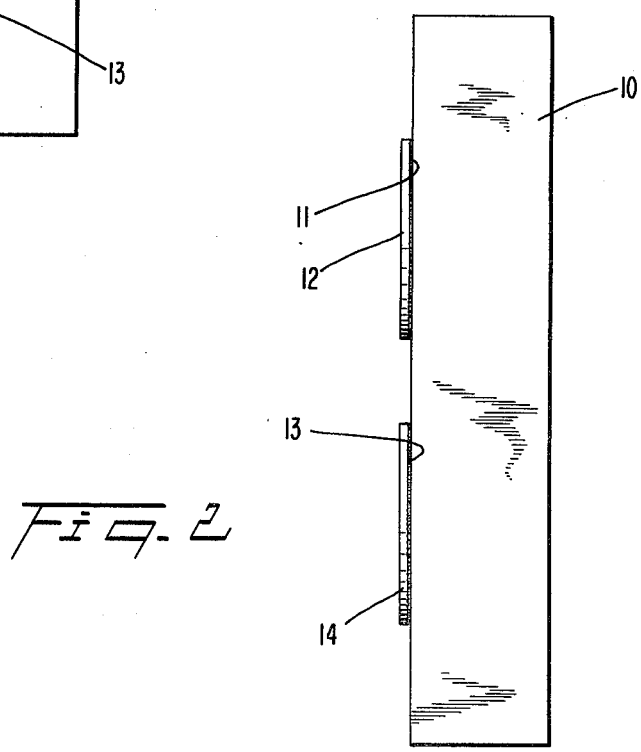

A suitable surface upon which antibody may be immobilized should have the property of having a large surface area exposed to the environment, relative to the volume occupied by the structure. It should be in the form of a unitary, integral structure capable of retaining its structural integrity for at least 24 hours of immersion in an aqueous or nonaqueous medium, depending on where the antigen is to be found.

Macroporous materials constructed of woven, wound, or compacted fibers may be employed in fabricating a suitable carrier in accordance with one embodiment of the invention. Sponges and open-cell foams of natural or synthetic material may also be employed. Microporous materials are preferred because of the large surface area exposed within the structure.

When microporous materials are employed, the method of immobilizing antibody thereon must be such that the antibody becomes immobilized on both internal and external surfaces of the structure, while retaining its activity. This procedure insures that the immobilized material is capable of binding not only soluble antigen that is in solution and that is capable of entering the pores of the microporous structure, but also antigens found on larger structures such as intact cells, cysts, and cell fragments that may be incapable of entering the pores.

A microporous structure is here defined as one having pores that fall within the size range from 25 nanometers to about 25 micrometers, and preferably, from 25 nanometers to 14 micrometers. In the most preferred embodiment of the invention, a microporous membrane filter is employed that has from about 70% to about 80% of its total volume as pores of substantially uniform size averaging 3 micrometers in diameter, in making the carrier.

Antibody molecules may be attached to a surface of the type described by any of a variety of methods known in the art. See Silman, I. H. and Katchalski, E., in *Annual Review of Biochemistry*, Vol. 35, p. 873 (1966); Melrose, G. J. H., in *Reviews of Pure and Applied Chemistry*, Vol. 21, p. 83 (1971); and Cuatrecasas, P. and Anfinsen, C. B., in *Methods in Enzymology*, Vol. 22 (1971). Such methods include covalent coupling, direct adsorption, physical entrapment and attachment to a protein-coated surface. Attachment to a protein-coated surface is the method of the preferred embodiment of the invention. In this method, the surface is first coated with a water-insoluble protein such as zein, collagen, fibrinogen, keratin, glutelin, polyisoleucine, polytryptophan, polyphenylalanine, polytyrosine, copolymers of leucine with p-amino phenylalanine, or other proteins that are essentially water-insoluble, but that are capable of forming a coating on the surface of a porous, and preferably microporous, carrier.

In the preferred embodiment, a microporous membrane filter is soaked in a solution of zein dissolved in an appropriate mixture of organic solvents. After soaking, the filter is removed and air dried. The zein is deposited on the internal and external surfaces in a thin, water-insoluble coating. When coated in this fashion, the volume of the membrane filter devoted to pores is reduced by only 5% to 10%, so that after coating, the microporous properties of the filter and its high ratio of surface area to volume are retained. Attachment of antibody is then accomplished simply by allowing the coated filter to contact an aqueous solution of the antibody, and drying. The method of attachment just described is essentially that of Lai et al, as described in U.S. Ser. No. 684,746. The immobilized antibody remains immunochemically reactive for long periods of time, particularly if air dried and stored under refrigeration.

The antibody used in the invention may be prepared by standard techniques well known in the art. Laboratory animals, such as rabbits, may be immunized against an antigen by serial exposure to the antigen, as by injection. Antibody may be prepared from the serum of immunized animals and partially purified by salt fractionation of the serum. An animal is here defined as immunized against an antigen if its serum contains antibody capable of immunochemically binding the antigen. Antibody preparations made by the salt fractionation of serum are in fact a mixture of antibodies, some directed against the antigen to be detected, and others directed against other antigens which the animal may have encountered. Control antibody preparations may be made in the same fashion, from the serum of animals which have never been immunized against the antigen to be detected. A control antibody preparation contains the same general mixture of antibodies, except that antibody capable of binding the specific antigen to be detected is absent.

The conjugate of antibody with enzyme is made using techniques known in the prior art. See Avrameas, S. and Uriel, J., in *Comptes Rendus Hebdomadaires des Seances de l'Academic des Sciences*, Vol. 262, p. 2543 (1966); Nakane, P. K. and Pierce, G. B., in *Journal of Histochemistry and Cytochemistry*, Vol. 14, p. 929 (1966); Nakane, P. K., in *Methods in Enzymology*, Vol. 37, p. 133 (1975). In an El-1 type of assay such as that employed in the present invention, the antibody moiety of the conjugate should have the same immunological specificity as the immobilized antibody. The enzyme moiety may be any enzyme capable of catalyzing a reaction which can be detected.

In the detection of antigens in feces, it is convenient to use an enzyme that is capable of mediating a color change in a chromagen, either by direct catalytic action upon the chromagen or by a coupled reaction. Preferably, the chromagen should be one that is only faintly colored in the unreacted state, and that becomes deeply colored only as a result of the enzyme-catalyzed reaction. The term "chromagen" is used to denote a substance having the property of becoming colored as a result of the enzyme-catalyzed reaction. Where the test result is to be measured by the color that is developed, it is advantageous if the chromagenic substance used is poorly soluble in the reaction solvent or is preferentially adsorbed to the filter matrix in the colored state. Reactions giving rise to a blue or green color should be avoided since there is also staining due to bile salts in the feces which can interfere with interpretation of color changes in the blue and green part of the spectrum.

In the preferred embodiment, the conjugate is formed of antibodies to *Entamoeba histolytica* coupled to peroxidase. Peroxidase is capable of catalyzing the oxidation of a variety of chromagenic substances in the presence of hydrogen peroxide. In the most preferred embodiment, 3-amino-9 ethyl carbazole is employed as the chromagen.

In applying the invention, the initial step involves bringing the immobilized antibody into contact with the specimen of feces. Depending upon the condition of the stool sample, whether formed or watery, dilution may or may not be required. The preparation should be sufficiently fluid to permit uniform distribution of antigen throughout its volume. Techniques, such as zinc sulfate flotation for concentrating the protozoa and removing solids, may be employed, but are not essential to the optimal practice of the invention.

In the detection of *Entamoeba histolytica* antigen, samples of feces as small as one gram are adequate for routine analysis although the lower limit of sample size has not been determined. The practical lower limit on the sample size is dictated, not by sensitivity limits on the assay, but by the fact that the antigen is not always homogeneously distributed in the feces. As the sample size is decreased, the likelihood of selecting a specimen lacking antigen is increased. A sample size of one gram has been determined to be a practical lower limit, given the need for reliability in a diagnostic test. In order to insure liberation of antigen from clumps of feces, the specimen should be well suspended in a diluent, such as water, by vigorous shaking and, if necessary, by the use of a stirring rod to disperse the clumps. Analysis may also be performed on materials obtained by direct aspiration of the rectum and sigmoid colon.

The simplest method of bringing the immobilized antibody into contact with the specimen is by simple immersion in an aqueous slurry of the specimen. This may be conveniently accomplished using a holder of inert material for the carrier on which the antibody is immobilized. The immobilized antibody is then incubated with the slurry of the specimen for a time sufficient to permit the occurrence of an immunochemical reaction between the antibody and any antigen in the specimen.

Referring now in detail to the drawing by numerals of reference, the numeral 10 denotes a wooden or plastic holder. A reactive membrane 12 is secured on the holder by small spots of an adhesive 11. This membrane 12 is a disc cut from a sheet of microporous cellulose mixed esters, having a nominal pore size of 3 microns and a porosity of 70-80%. Its external and internal surfaces are covered with a thin film of zein, and an antibody capable of immunochemically binding the antigen to be detected is immobilized in the zein.

The second membrane 14 is a control. It is also a disc cut from the same material as the membrane 12, and is secured to the holder 10 by small spots of an adhesive 13. The membrane 14 is similarly coated with zein, but the antibody that is immobilized on the second membrane 14 is incapable of immunochemically binding the antigen that is to be detected.

The parameters of incubation time and incubation temperature are interdependent, and may be modified to meet specific requirements of sensitivity, speed, and convenience. Temperatures ranging from 15° C. to 45° C. may be employed, and temperatures in the range 25° C. to 35° C. are preferred. The use of higher temperatures tends to increase the rate of reaction so that correspondingly shorter times are required to achieve a desired result. Where the maximum operating convenience is desired, room temperature may be employed. Since room temperature may vary from about 20° C. to 40° C., depending upon the climate, heating or air conditioning, the reaction time chosen must be long enough to allow the reaction to proceed to a sufficient extent even at the lowest temperature likely to be encountered. In using the invention for the detection of antigens of *Entamoeba histolytica*, an overnight incubation gives satisfactory results.

During the incubation, any antigen that is capable of binding immunochemically to the immobilized antibody will be bound. Because of the tight binding that occurs in immunochemical reactions, the bound antigen remains bound to the immobilized antibody during washing procedures, under most mild conditions of temperature, pH and ionic strength, in the absence of chaotropic ions. It has been found that a brief water rinse to remove particulate contamination, followed by immersion in buffer for one hour, is a satisfactory washing procedure.

The next step involves the immunochemical reaction between the bound antigen and the antibody-enzyme conjugate. Conditions of buffer, time, and temperature are those used for carrying out immunochemical reactions generally. In the preferred embodiment, conjugated peroxidase activity ranging from 2 units/ml to 4 units/ml is incubated with the bound antigen, in a solution containing 50% w/v fetal calf serum, tris-saline buffer pH 8.0 for two hours to four hours at ambient temperature. The addition of fetal calf serum is recommended to suppress non-specific binding of conjugate to the coated membrane filter during the incubation. At the end of the incubation, the sample may be washed in similar fashion to the previous washing, in order to remove any antibody-enzyme conjugate that has not reacted. The reaction surface of the membrane 12 now has conjugate immunochemically bound to it, at sites occupied by the antigen that has been harvested from the fecal slurry.

The sample is then placed in a suitable reaction buffer containing a substrate for the enzyme moiety of the conjugate. Progress of the enzymic reaction is followed by any method appropriate to the particular combination of enzyme and substrate chosen. Where the enzyme is peroxidase, hydrogen peroxide and a suitable chromagenic substrate are allowed to react, catalyzed by the enzyme, to produce a visable color change. In the preferred embodiment, the oxidized dye will color the membrane to which the enzyme is bound. The presence of dye stain indicates that antigen is bound thereto and hence that antigen was present initially in the fecal sample. The absence of stain indicates the absence of antigen in the stool sample.

There are a number of potentially interfering factors. In any immunochemical reaction where it is desired to measure or detect a specific antigen, false positives can result if there are cross-reacting antigens present. Such antigens usually have a close structural relationship with the antigen to be detected, and often come from organisms biologically related to the pathogen in question. Such cross-reacting antigens have not been found to exist to any significant degree in the practice of the preferred embodiment. The antigens of nonpathogenic amoebae sometimes encountered in human feces, such as *Entamoeba coil*, do not significantly cross-react with *Entamoeba histolytica* in the described invention. Indeed, this lack of cross-reactivity is in part responsible for the great selectivity of the assay, making it possible to distinquish *Entamoeba histolytica* from other amoebae with greater speed and accuracy than was heretofore possible.

No significant interference with the practice of the preferred embodiment has been found, arising from substances that might inhibit an immunochemical reaction. Some non-specific interference may be found due to degradation of antigen by proteolytic enzymes that may occur in a fecal sample. Such interference may be effectively eliminated by the addition of 6-amino caproic acid, a competitive inhibitor of a wide variety of proteolytic enzymes.

A low level of non-specific adsorption to a membrane that is exposed to a suspension of feces can occur. Interfering adsorbents include colored substances such as bile salts, peroxidase of cellular or bacterial origin, and antigens bindable to non-*Entamoeba histolytica* immobilized antibodies. For this reason, the practice of the invention includes the use of a control, having immobilized non-*Entamoeba histolytica* antibodies and treated identically to the test sample in the assay steps. A background color may be developed in the control, which serves as a basis of comparison for the test sample. Factors which contribute to reducing the background color include: (1), where a protein-coated surface is used to immobilize antibody, the non-specific binding of fecal peroxidases is minimized by maximizing the amount of antibody protein immobilized on the coating, such that the capacity of the coating to bind additional protein is minimized; (2), since most interfering colored substances are brown, green or blue, the use of a chromagen yielding a red color after enzymic conversion is recommended; and (3), careful washing to move unbound substances reduces background color development. The immunochemical binding of other antigens in feces to the control and test samples is minimal and in any event does not interfere with qualitative determinations of the type practiced in the preferred embodiment.

During incubation of coated surfaces having immobilized antibody and immunochemically bound antigen with the antibody-enzyme conjugate, it is desirable to minimize non-specific binding of conjugate to the coated surface. This may be accomplished, for example, by including fetal calf serum in the conjugate solution, to competitively reduce non-immunochemical binding of conjugate to the coated surface.

The invention will now be demonstrated by the description of certain specific examples of its practice. In these examples, and elsewhere in the specification, unless expressly stated otherwise, all temperatures are Centigrade and all parts and percentages are by weight.

EXAMPLE I

Detection of the Antigen of *Entamoeba histolytica*

A. Preparation of the Carrier

A zein-coated membrane filter capable of immobilizing antibody on its surface was prepared as follows. A solution containing 7.9 grams of zein dissolved in a solvent mixture of 18 ml. ethanol, 34 ml. n-butanol, 8 ml. water, and 3 ml. Cellosolve (Trade Mark, Union Carbide Corp., New York, N.Y.) was prepared at room temperature. A microporous membrane filter having a 3 $\mu$m average pore size (Type SS filter, manufactured by Millipore Corp., Bedford, Massachusetts) and a thickness of about 150 $\mu$m was immersed in the zein solution and allowed to soak for approximately 24 hours at room temperature.

A membrane filter coated in the above-described manner contains a thin coating or film of zein covering the internal and external surfaces of the filter. Prior to coating, such filters are 70–75% porous. After coating, they are 58–64% porous, indicating that the zein coating is very thin in relation to the pore size. Calculations based on pore size and photomicrographic measurement of the internal structure of the coated membrane indicate that the total surface area exposed within the pores is approximately 250 times the external surface area. Hence, a filter disc 2.5 cm in diameter has a calculated approximately 1130 cm$^2$ of internal surface that is exposable to reactants.

B. Immobilization of Antibody

Rabbit antibody against *Entamoeba histolytica*, strain HK-9, was obtained from a commercial source (ICN Pharmaceuticals, Inc., Irvine, Calif.). The antibody was immobilized on the coated surface by incubating a coated membrane filter immersed in a solution of antibody (20 mg/ml–25 mg/ml in .01 M Potassium phosphate and 0.15 M Sodium Chloride, pH 7.0) at 4° C. overnight. After the incubation, the filter was air dried at room temperature then washed once with MilliRO TM water and air dried at room temperature. Antibody bound in this manner to the surface of a coated filter remains immunochemically reactive for at least 9 months, under storage at 4° C.

C. Conjugate Preparation

A conjugate of rabbit antibody against *Entamoeba histolytica* strain HK-9, with horseradish peroxidase type II or type VI (Sigma Chemical Corp., St. Louis, Mo., or essentially equivalent preparations, HPOD and HPOFF, respectively, from Worthington Biochemical Corporation, Freehold, New Jersey) was formed. The type II peroxidase had a specific activity of 400 units/mg–900 units/mg, type VI has 3,000 units/mg–4,000 units/mg, a unit of enzyme activity of being defined as that amount which decomposes 1 $\mu$mole $H_2O_2$/min at 25° C. pH 7.0. The antibody was described in Example I/B.

The metaperiodate activation method of conjugate formation was employed, generally as described by Nakane, P. K. and Kawaoi, A., in J. Histochem. Cytochem., vol. 22, p. 1084, (1974). The conjugate preparation was stored at 4° C. at a total protein concentration of 3.3 mg/ml.

D. Detection of Antigen in a Stool Sample

A sample of feces weighing 10 gms–30 gms was added to a buffer solution containing 0.01 M tris (2-amino-2-hydroxymethyl-1,3-propanediol) and 0.15 M sodium chloride, at pH 8.0. The sample container was tightly closed and the sample was dispersed by vigorous shaking, by hand or mechanized means, for 10 minutes. After shaking, the sample container was opened. The membrane filter, having antibody against *Entamoeba histolytica* immobilized on its surfaces, prepared as described above, was immersed in the sample. A control membrane filter, having normal antiserum immobilized on its surfaces (specifically lacking antibody against *Entamoeba histolytica*) was also immersed. For convenience, both filters were mounted on a suitable holder (as shown in the drawing to facilitate immersion and removal of the filters and to minimize fecal contamination of the laboratory environment. The holder was allowed to remain immersed in the sample overnight at ambient temperature.

The holder was then removed from the sample, rinsed briefly with tap water, and then immersed in 0.01 M tris, 0.15 M sodium chloride, pH 8.0 for one hour. This procedure removed unbound antigen from the filter surfaces, but did not interfere with the attached, immunochemically bound antigen.

The holder was then placed in a test tube, to which was added 5 ml of antibody-enzyme conjugate containing 11 $\mu$g/ml total protein. The conjugate was prepared with type II or HPOD peroxidase as described above, and diluted 300-fold, just prior to use, in 50% fetal calf serum. The filter was allowed to incubate for 4 hours at ambient temperature, immersed in the conjugate solution.

Unbound conjugate was removed by immersing the filter for one hour in 0.01 M tris, 0.15 M sodium chloride, pH 8.0. The filter was then removed from the wash and placed in the staining reagent for a 10-minute incubation at ambient temperature. The staining reagent was composed of a mixture of 10 mg 3-amino-9-ethyl carbazole, 6 ml dimethyl sulfoxide, 50 ml 0.02 M sodium acetate pH 5.0, and 6 ml 3% (v/v) hydrogen peroxide.

The binding of conjugate was evidenced by a red color due to the oxidation of aminoethyl carbazole catalyzed by the peroxidase in the presence of hydrogen peroxide. Since binding of conjugate is dependent on the prior binding of antigen to the immobilized antibody, a red color is observed only if there was antigen present initially in the fecal sample. The control filter lacking immobilized antibody against *Entamoeba histolytica* failed to bind antigen and therefore failed to bind conjugate. The control therefore remained unstained by the dye, and served as a reference for purposes of color comparison with the test filters. Such a reference is worthwhile because a certain amount of non-specific staining will be encountered after immersion in the fecal sample, and also because it is easier to identify a weakly positive test, faintly stained, by comparison with a control.

The effectiveness of the method was tested in fecal samples that were also examined microscopically by direct examination and in stained preparations. All samples having microscopically identified *Entamoeba histolytica* trophozoites or cysts gave a positive reaction when assayed according to the method of Example I/D. In addition, samples identified as having the following parasite composition have given a negative reaction using the method of the example: *Entamoeba hartmanii, Entamoeba coli, Endolimax nana, Giardia lamblia, Chilomastix mesnili, Iodamoeba butschlii,* combinations of the foregoing, post-treatment samples, microscopically negative samples and samples classed as atypical Entamoeba species. Some samples lacking microscopically demonstrable *Entamoeba histolytica* nevertheless gave a positive reaction when tested according to the example. Where follow-up samples were obtainable, the presence of *Entamoeba histolytica* was eventually confirmed in a number of cases. Also, where multiple specimens were submitted, the results obtained using the present invention were more consistent than microscopic examination results. The occurrence of actual false positives (a positive test result in the demonstrated absence of *Entamoeba histolytica*) has not been observed. Indeed, with current methodology, it would be difficult to do so, since the standard tests are evidently less sensitive than the present invention. The results are summarized below:

| Microscopic Identification | No. Cases Presented | No. of Cases Positive for *Entamoeba histolytica* by Method of Example 1 |
|---|---|---|
| *E. histolytica* present | 22 | 22 |
| *E. histolytica* absent | 72 | 7* |
| *E. histolytica* absent initially but present in follow-up samples | 4 | 4 |

*Remarks - Microscopic identification - 2 atypical *E. histolytica* 2 *E. hartmanii* 2 *Giardia lamblia* 1 negative
This number includes cases in which follow-up samples confirmed the presence of *E. histolytica* in the patient's digestive tract.

Example 2

Alternative Method for Detecting an Antigen in a Stool Sample

A fecal speciman weighing 2–3 gms was placed in a container which could be capped, diluted with 40 ml of tris-saline buffer, capped and shaked vigorously to produce a homogenous suspension. (Tris-saline buffer contained 4.44 gms tris-hydrochloride, 2.65 gms tris base, 8.83 gms sodium chloride, 10 gms 6-amino caproic acid and 0.1 gms Thimerosal, dissolved in 1 liter of distilled water. The resulting pH was 8.0. Tris is 2-amino-2-hydroxymethyl-1,3-propanediol.)

A pair of membrane filters, a test filter having immobilized antibody against *E. histolytica* and a control having immobilized normal antibody, prepared as described in Example 1 and mounted on a suitable carrier, were immersed in the suspension. The filters remained immersed in the suspension overnight at ambient temperature.

After the overnight incubation, the carrier bearing the filters was removed and washed thoroughly under tap water, with care taken to avoid rupturing the filters.

The filters were then transferred to a shallow tray containing a solution of antibody-peroxidase conjugate, the solution depth being sufficient to completely cover the filters. The conjugate solution contained 11 μg/ml total conjugate protein, which included 4 units/ml peroxidase activity, dissolved in 50% fetal calf serum and tris-saline buffer. Preparations of conjugate solution may be lyophilized and remain stable upon storage at 4° C. for at least 12 months. They may be reconstituted 15 minutes to 20 minutes prior to use by the addition of distilled water. Test and control filters were incubated with the conjugate solution for 2 hours at ambient temperature with occasional gentle agitation to remove any bubbles trapped on the filter surface.

The carrier was then removed from the tray, and the filters carefully rinsed with tap water, followed by immersion for 1 hour in 100 ml tris-saline buffer.

The filters were next incubated with substrate solution. The substrate solution was prepared immediately prior to incubation by dissolving 15 mg 3-amino-9-ethyl carbazole in 6 ml dimethylsulfoxide, then adding 50 ml of acetate buffer containing 0.6 ml 3% (v/v) hydrogen peroxide. The acetate buffer contained 2.72 gms sodium acetate, 0.54 gms succinic acid and 0.1 gms Thimerosal dissolved in 1 liter of distilled water. The filters were placed in a 16 mm×100 mm test tube containing 8 ml freshly prepared substrate solution and incubated for 10 minutes at ambient temperature.

Following a final wash by immersion in tris-saline buffer, the results of the test could be read. A positive result (antigen of *Entamoeba histolytica* present in the fecal sample) was indicated by the appearance of red stain on the test filter, in contrast with the control.

This procedure presents improvements in operating convenience and sample readability.

General Concluding Remarks

The present invention relates to the detection of an antigen in feces using an immunochemical reaction of the EL-1 type. The invention has been applied to the detection and diagnosis of *Entamoeba histolytica* infection.

Because such infections are widespread, yet difficult to diagnose, and especially prevalent in underdeveloped areas of the world, there is great need for a simple, inexpensive and reliable diagnostic method. The present invention represents a significant advance over the prior art with respect to all three of these needed attributes. It offers in addition the potential for detecting asymptomatic carriers of *Entamoeba histolytica* infection. The progress of chemotherapy may be monitored, to reduce toxic side reactions. The invention is further adaptable to the detection of antigens in clinical material other than feces, such as in liver abcesses due to secondary invasion by the amoeba. The method is also applicable to the diagnosis of other parasitic infections, such as infections by *Giardia lamblia*. Broadly speaking, the technique is adaptable to detect antigens found in a wide variety of conditions, including non-aqueous media.

While the invention has been described in connection with specific embodiments thereof, it will be understood that it is capable of further modifications and this application is intended to cover any variations, uses, or adaptations of the invention following in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method for detecting the presence of a diagnostic antigen in an unfractionated sample of feces or colon aspirate dispersed in a liquid, comprising:

immersing in the sample first and second microporous membranes each of which has a network of voids permitting liquid flow therethrough, the first membrane being a test membrane and having immobilized to its external and internal surfaces a first antibody which is specifically immunochemically reactive with said antigen, the second membrane being a control membrane having immobilized on its external and internal surfaces a second antibody which is immunochemically non-reactive with said antigen, said membranes having capillary pore sizes in the range from about 25 nanometers to 25 micrometers and having a thin, water-insoluble coating of an inert proteinaceous material on their surfaces, said antibodies being immobilized to said coatings, said first and second membranes being immersed together in the sample and being treated essentially identically in all steps:

incubating the membranes in said sample to permit immunochemical reaction between the immobilized antibody of the first membrane and the antigen to be detected;

washing the membranes to remove non-specifically bound materials;

immersing the membranes in a serum diluted solution of a conjugate of an enzyme and an antibody to the antigen to be detected, in order to immunochemically bind the conjugate to any of said diagnostic antigen bound to said first immobilized antibody on the test membrane;

again washing the membranes to remove non-specifically bound materials;

thereafter testing the membranes for any activity of the enzyme moiety of the conjugate bound thereto; and comparing the first and second membranes for evidence of enzyme activity, any substantial difference being indicative of the presence of the diagnostic antigen in the sample.

2. The method of claim 1 wherein said coating is zein or collagen and the microporous membranes have pore sizes in the range of about 25 nanometers to 14 micrometers.

3. The method of claim 2 wherein the enzyme moiety of the conjugate is peroxidase, and the peroxidase activity is tested by supplying a source of hydrogen peroxide and a chromogenic substrate whose oxidized form is visible in the microporous membrane.

4. The method of claim 2 wherein at least a portion of said diagnostic antigen is a particulate antigen substantially insoluble in the liquid of said sample.

5. The method of claim 2 wherein said diagnostic antigen is an antigen of *Entamoeba histolytica*.

6. The method of claim 3 wherein said diagnostic antigen is of *Entamoeba histolytica* and the oxidized form of said chromgenic substrate is water-insoluble.

7. A device for use in detecting a diagnostic antigen in an unfractionated sample of feces or colon aspirate in a liquid, said device comprising a support member having first and second microporous membranes attached thereto in an arrangement so that both membranes can be immersed together in said unfractionated sample, the membranes having a network of capillary pores therethrough so that upon immersion in the sample, the sample contacts the membranes and the liquid penetrates the membranes and makes contact with the surfaces defined by the network of capillary pores therein, said membranes having capillary pore sizes in the range from about 25 nanometers to 25 micrometers and having a thin, water-insoluble coating of an inert proteinaceous material on their external and internal surfaces, the first membrane being a test membrane having immobilized on the proteinaceous coating on the external and internal surfaces thereof an antibody which is specifically immunochemically reactive with the diagnostic antigen in the unfractionated feces or colon aspirate, the second membrane being a control having immobilized on the protein aceous coating on the external and internal surfaces thereof a second antibody which is immunochemically non-reactive with the diagnostic antigen in the unfractionated feces or colon aspirate, whereby upon immersion of the membranes in the sample, the diagnostic antigen becomes preferentially bound to the test membrane by immunochemical binding, and non-specifically bound materials may be washed from the membranes.

8. A device according to claim 7 wherein said proteinaceous material coating said membranes comprises zein or collagen.

9. A device according to claim 8 wherein said diagnostic antigen is an antigen of *Entamoeba histolytica*.

10. A test kit comprising the device of claim 7, a conjugate of an enzyme and an antibody which is capable of binding immunochemically with the diagnostic antigen to be detected, and a test mixture for detecting the presence of said enzyme which comprises a chromogen which produces a visible color change in the presence of said enzyme.

11. A test kit according to claim number 10 wherein said test mixture further includes a source of hydrogen peroxide, said enzyme comprises peroxidase, and said kit includes calf serum for addition to said conjugate.

* * * * *